(12) United States Patent
Juárez Paz

(10) Patent No.: US 11,707,622 B2
(45) Date of Patent: Jul. 25, 2023

(54) AUTOMATIC DETERMINATION OF INPUTS FOR CLOSED-LOOP ALGORITHMS FOR OPTIMIZATION OF STIMULATION PARAMETERS

(71) Applicant: Boston Scientific Neuromodulation Corporation, Valencia, CA (US)

(72) Inventor: León M. Juárez Paz, Berlin (DE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 170 days.

(21) Appl. No.: 17/137,110

(22) Filed: Dec. 29, 2020

(65) Prior Publication Data

US 2021/0196956 A1   Jul. 1, 2021

Related U.S. Application Data

(60) Provisional application No. 62/955,802, filed on Dec. 31, 2019.

(51) Int. Cl.
*A61N 1/00* (2006.01)
*A61N 1/36* (2006.01)
(Continued)

(52) U.S. Cl.
CPC ..... *A61N 1/36067* (2013.01); *A61N 1/36171* (2013.01); *A61N 1/36175* (2013.01);
(Continued)

(58) Field of Classification Search
None
See application file for complete search history.

(56) References Cited

U.S. PATENT DOCUMENTS

| 8,768,453 B2 | 7/2014 | Parramon et al. |
| 9,119,964 B2 | 9/2015 | Marnfeldt |

(Continued)

FOREIGN PATENT DOCUMENTS

WO   2010/109448 A1   9/2010

OTHER PUBLICATIONS

Kuo, Chao-Hung, et al., "Approaches to Closed-Loop Deep Brain Stimulation for Movement Disorders," Neurosurgical Focus, vol. 45, Aug. 2018, 10 pages.

(Continued)

*Primary Examiner* — John R Downey
*Assistant Examiner* — Anant A Gupta
(74) *Attorney, Agent, or Firm* — Lewis & Reese, PLLC

(57) ABSTRACT

Methods and systems for facilitating the determining and setting of stimulation parameters for programming an electrical stimulation system are disclosed. The disclosed systems and methods use algorithms to identify patient-specific metrics to use as feedback variables for optimizing stimulation parameters for a patient. The patient-specific metric(s) are determined by ranking a plurality of clinical indicators for the patient with and without the presence of a medical intervention to determine which clinical indicators respond most strongly to the medical intervention. The clinical indicators that respond most strongly can be used as the patient-specific metric for optimizing stimulation, or a composite patient-specific metric may be derived as a mathematical combination of a plurality of clinical indicators that respond well to the intervention.

20 Claims, 13 Drawing Sheets

(51) Int. Cl.
    *G16H 20/40*    (2018.01)
    *G16H 50/30*    (2018.01)
    *A61N 1/372*    (2006.01)

(52) U.S. Cl.
    CPC ..... *A61N 1/36192* (2013.01); *A61N 1/37252* (2013.01); *G16H 20/40* (2018.01); *G16H 50/30* (2018.01)

(56) References Cited

U.S. PATENT DOCUMENTS

| | | |
|---|---|---|
| 2007/0255346 A1 | 11/2007 | Rondoni et al. |
| 2011/0208264 A1* | 8/2011 | Gliner ................ A61N 1/36185 607/45 |
| 2013/0184794 A1 | 7/2013 | Feldman et al. |
| 2014/0277284 A1 | 9/2014 | Chen et al. |
| 2018/0104500 A1 | 4/2018 | Blum et al. |
| 2018/0264278 A1 | 9/2018 | Laghi |
| 2019/0143120 A1* | 5/2019 | Sinclair .............. A61N 1/36067 607/45 |

OTHER PUBLICATIONS

Parastarfeizabadi, Mahboubeh, et al., "Advances in Closed-Loop Deep Brain Stimulation Devices," Journal of Neuroengineering and Rehabilitation, 2017, 14:79, 20 pages.

International Search Report and Written Opinion regarding corresponding PCT Application No. PCT/US2020/067367, dated Mar. 30, 2021.

* cited by examiner

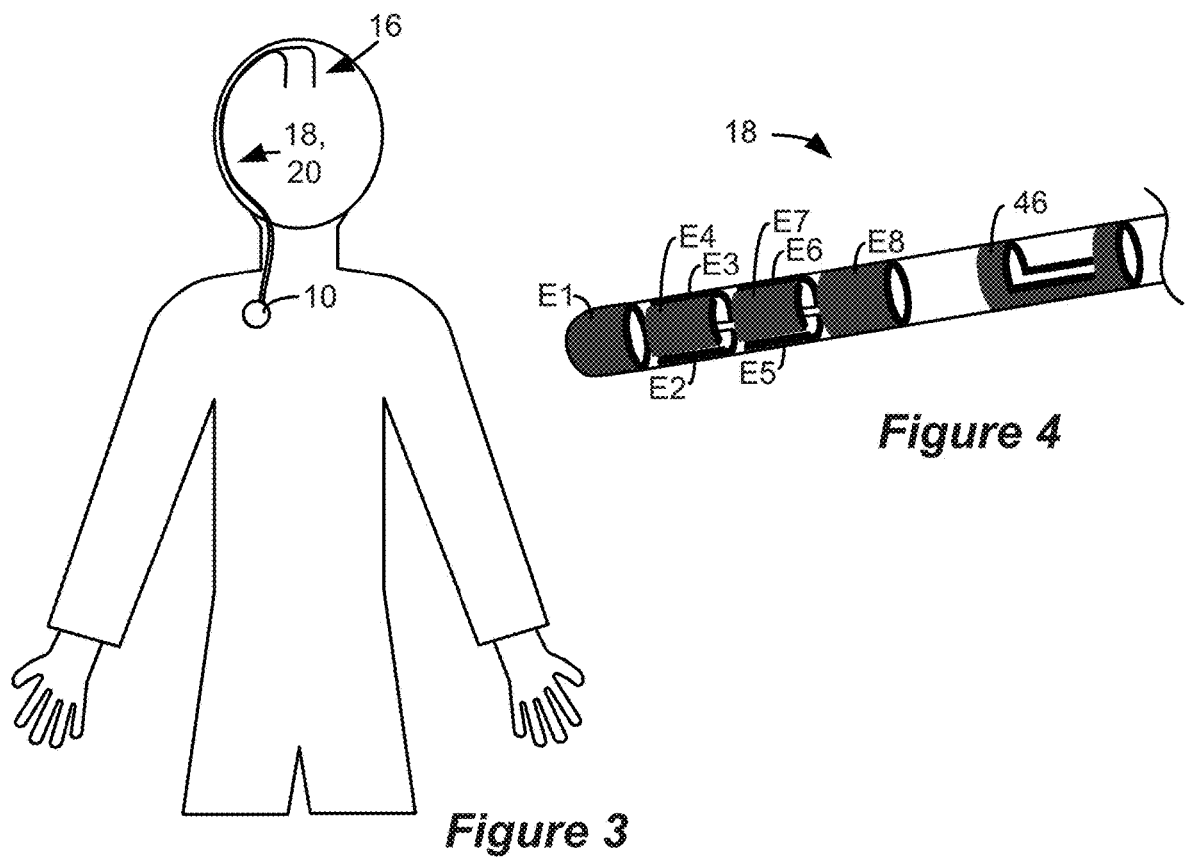
Figure 3
Figure 4
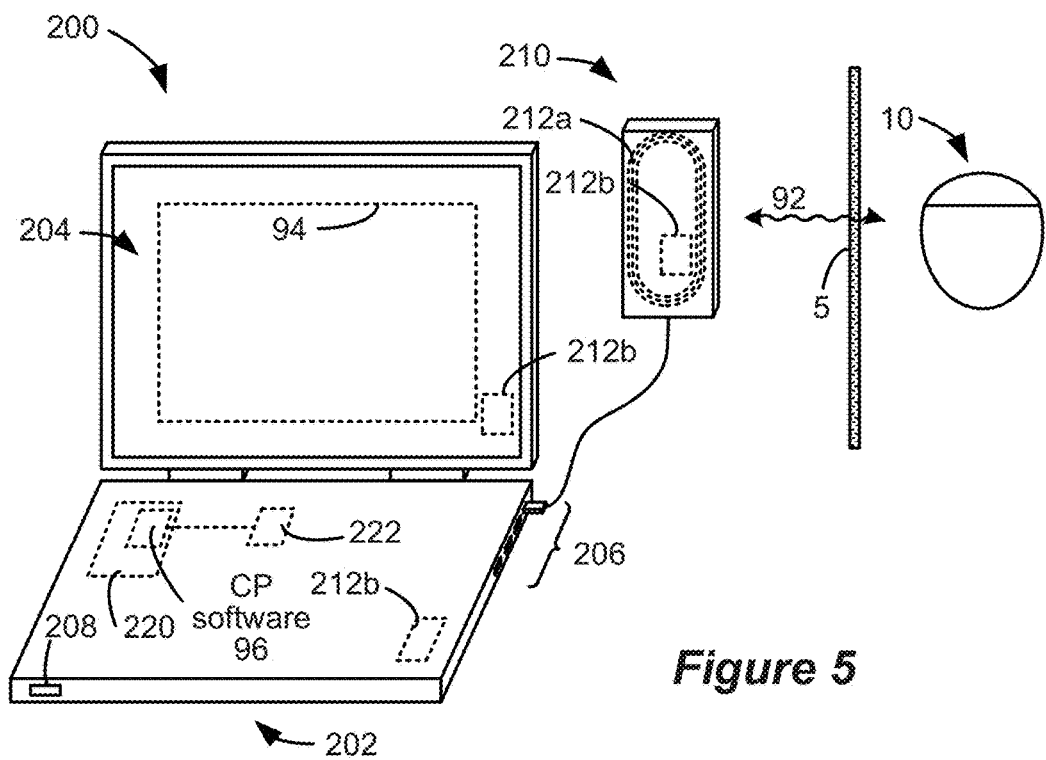
Figure 5

| Patient Response (Clinical Indicator) | Rank T-OFF | Rank T-ON | Weight |
|---|---|---|---|
| Speech | 3 | 1 | 0.333 |
| Facial Expression | 3 | 1 | 0.333 |
| Tremor face | 2 | 0 | 0.500 |
| Tremor Right Upper Extremity | 2 | 0 | 0.500 |
| Tremor Left Upper Extremity | 0 | 0 | |
| Tremor Right Lower Extremity | 3 | 2 | 0.083 |
| Tremor Left Lower Extremity | 0 | 0 | |
| Postural Tremor Right Upper Extremity | 0 | 0 | |
| Postural Tremor Left Upper Extremity | 0 | 0 | |
| Rigidity Neck | 2 | 0 | 0.500 |
| Rigidity Right Upper Extremity | 2 | 0 | 0.500 |
| Rigidity Left Upper Extremity | 1 | 0 | 0.250 |
| Rigidity Right Lower Extremity | 0 | 0 | |
| Rigidity Left Lower Extremity | 0 | 0 | |
| Finger Taps Right | 2 | 1 | 0.125 |
| Finger Taps Left | 2 | 0 | 0.500 |
| Hand Grasps Right | 2 | 1 | 0.125 |
| Hand Grasps Left | 2 | 0 | 0.500 |
| Leg Agility Right | 1 | 0 | 0.250 |
| Leg Agility Left | 1 | 0 | 0.250 |
| Posture | 1 | 0 | 0.250 |
| Gait | 3 | 2 | 0.083 |
| Postural Stability | 0 | 0 | |
| Body Bradykinesia and Hypokinesia | 3 | 1 | 0.333 |
| Sensor Tremor Right Upper Extremity | 0 | 0 | |
| Sensor Tremor Left Upper Extremity | 0 | 0 | |
| Sensor Finger Taps Right Amplitude | 2.8 | 1.9 | 0.072 |
| Sensor Finger Taps Left Amplitude | 2.4 | 1.1 | 0.176 |

*Figure 10*

Patient ID  A-1234

Medication State  Off

Time since last Medication Dose  12 Hours  00 Minutes

Patient Responses to Assess with Sensor

☐ Finger Tapping
☐ Hand Grasping
☐ Hand Alternating
☐ Arm Postural Tremor
☐ Arm Kinetic Tremor
☐ Arm Rest Tremor

*Figure 11C*

Assign Clinical Indicators and Weights For Composite Patient-Specific Metric

1200

Right Body Side Symptoms          Weight

1) Finger Tapping (Sensor) ▶      0.750

2) Arm Rigidity ▶                 0.250

+ Add Symptom

*Figure 12*

AUTOMATIC DETERMINATION OF INPUTS FOR CLOSED-LOOP ALGORITHMS FOR OPTIMIZATION OF STIMULATION PARAMETERS

CROSS REFERENCE TO RELATED APPLICATIONS

This is a non-provisional of U.S. Provisional Patent Application Ser. No. 62/955,802, filed Dec. 31, 2019, which is incorporated herein by reference in its entirety, and to which priority is claimed.

FIELD OF THE INVENTION

This application relates to methods and systems for providing neuromodulation, and in particular deep brain stimulation (DBS). More specifically, this application relates to methods and systems for automatically identifying optimal variables to use as inputs to algorithms for optimization of stimulation parameters.

INTRODUCTION

Implantable electrical stimulator devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will focus primarily on the use of the disclosed techniques within a Deep Brain Stimulation (DBS) system, such as is disclosed in U.S. Patent Application Publication No. 2013/0184794. However, the disclosed techniques may find applicability in the context of any implantable medical device or implantable medical device system.

As shown in FIG. 1, a DBS system typically includes an electrical stimulator, such as an implantable pulse generator (IPG) 10 (or an implantable medical device, more generally), which includes a biocompatible device case 12 that is formed from a metallic material such as titanium. The case 12 typically comprises two components that are welded together, and it holds the circuitry and battery 14 (FIG. 2) necessary for the IPG 10 to function. The battery 14 may be either rechargeable or primary (non-rechargeable) in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make electrical contact with the electrode terminals 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry couplable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a handholdable, portable housing.

External charger 50 provides power to recharge the IPG 10's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

In a DBS application, as is useful in the treatment of neurological disorders such as Parkinson's disease, the IPG 10 is typically implanted under the patient's clavicle (collarbone), and the leads 18 (or lead extensions) are tunneled through the neck and between the skull and the scalp where the electrodes 16 are implanted through holes drilled in the skull in the left and right sides of the patient's brain, as shown in FIG. 3. Specifically, the electrodes 16 may be implanted in the subthalamic nucleus (STN), the pedunculopontine nucleus (PPN), or the globus pallidus internus (GPi). Stimulation therapy provided by the IPG 10 has shown promise in reducing the symptoms of neurological disorders, including rigidity, bradykinesia, tremor, gait and turning impairment, postural instability, freezing, arm swing, balance impairment, and dystonia.

While FIG. 1 generically illustrates the electrodes 16 as aligned linearly along a lead 18, electrode leads 18 for DBS applications commonly include segmented electrodes that allow for directional control of stimulation. The electrode lead 18 in FIG. 4 includes multiple circumferential (or ring) electrodes and multiple segmented electrodes. In particular, electrodes E1 and E8 are circumferential electrodes that extend around the circumference of the lead 18 while electrodes E2-E7 are segmented electrodes. As used herein, segmented electrodes refer to electrodes that do not extend fully around the perimeter of an electrode lead 18. In the illustrated embodiment, the segmented electrodes are arranged with three electrodes at a particular axial position, each segmented electrode spanning an approximately 90-degree arc around the lead 18 with approximately 30 degree spaces between neighboring segmented electrodes. Although a particular example of a lead is illustrated in FIG. 4, the type and placement of electrodes 16 along a lead is application specific and therefore can vary. For example, a lead may include more or fewer segmented electrodes at a given axial position and more or fewer circumferential electrodes in addition to the segmented electrodes. As will be understood, because the segmented electrodes are separated by a non-conductive break, electrical stimulation that is directed to a segmented electrode propagates outward in the direction of the electrode rather than uniformly about the lead 18 as with circumferential electrodes. The lead 18 additionally includes a marker 46 that is aligned with segmented electrodes E2 and E5. The marker 46 provides a visual indication of the lead's orientation prior to implantation as well as a radiological indication of the lead's orientation after implantation.

As mentioned above, the electrical stimulation that the IPG 10 is capable of delivering is highly customizable with respect to selected electrodes, current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, the stimulation parameters that might provide effective stimulation therapy for a particular patient are typically determined using a trial and error approach. Thus, after the leads are implanted, an initial programming session is typically performed to customize the parameters of the stimulation provided by the IPG 10 to obtain the greatest benefit for the patient. While not common in DBS applications due to the dangers of having externalized leads or lead extensions, in other applications such as spinal cord stimulation (SCS), it is common for the initial programming session to be performed after lead implantation using an external trial stimulator that mimics the operation of the IPG 10 and that is coupled to the implanted leads 18 but is not itself implanted.

Referring to FIG. 5, the initial programming is typically performed by communicating different stimulation programs from a clinician's programmer system (CP System) 200 to the IPG 10 and observing the patient's responses to the IPG 10's execution of the different programs. For a DBS application, a clinician may observe the extent to which the current stimulation program decreases the effects of the patient's neurological disorder (e.g., the extent to which the stimulation program decreases the degree of tremor) as well as any side effects induced as a result of the stimulation program. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 5, CP computer 202 is shown as a laptop computer that includes typical computer user interface means such as a screen 204, a mouse, a keyboard, speakers, a stylus, a printer, etc., not all of which are shown for convenience.

Also shown in FIG. 5 is an accessory communication head 210 that is couplable to a port of the CP computer 202, such as a USB port 206, and that is specific to the CP computer 202's operation as a neurostimulator controller. Communication between the CP system 200 and the IPG 10 may communication schemes, such as Bluetooth, Bluetooth low energy (BTLE), or the like, or may comprise magnetic inductive or short-range RF telemetry schemes (as described above with respect to communications between the IPG 10 and the programmer 40), and in this regard the IPG 10 and the CP computer 202 and/or the communication head 210 (which can be placed proximate to the IPG 10) may include antennas compliant with the telemetry means chosen. For example, the communication head 210 can include a coil antenna 212*a*, a short-range RF antenna 212*b*, or both. The CP computer 202 may also communicate directly with the IPG 10, for example using an integral short-range RF antenna 212*b*, without the use of the communication head 210.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To test different stimulation parameters during the initial programming session, a user interfaces with a clinician programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer 202's non-volatile memory 220. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 cause the CP computer 202 to communicate the stimulation parameters to the IPG 10 using a suitable antenna 212a or 212b, either in the communication head 210 or the CP computer 202 as explained earlier. The CP software 96 enables a user to select the type of electrode lead(s) that have been implanted (e.g., from a list of leads that are configured in the software 96) and to customize the stimulation parameters using the available electrodes on the implanted lead. In this way, the user can communicate different stimulation parameters to the IPG 10 for execution to observe the effects of the various parameters and to home in on the appropriate settings for the patient.

After implantation, a clinician will program the implantable pulse generator using the clinician programmer, remote control, or other programming device. According to at least some programming techniques, the clinician enters stimulator parameters for a stimulation program and the stimulation program is used to stimulate the patient. The clinician observes the patient response. In at least some instances, the clinician asks the patient to describe, rate, or otherwise provide information about the effects of the stimulation such as what portion of the body is affected, how strong is the stimulation effect, whether there are side effects or negative effects, and the like.

In at least some instances, the clinician may be remote from the patient. For example, the clinician may be in another room, treatment or care facility, city, state, or even country. This may be advantageous as it can allow skilled clinicians to interact with patients that are remote from the clinician without requiring travel or loss of time by the clinician. As another example, the patient may be sent home after surgery and the clinician can program the device remotely while the patient is at home.

Such remote programming, however, may encounter difficulties such as, for example, limited bandwidth, speech impaired patients, deaf patients, patients who speak a different language from the clinician, noise over the phone or video connection between patient and clinician, patient difficulty hearing due to hearing aid devices, and the like.

In addition, current techniques for programming an electrical stimulation system are a tedious trial-and-error process which only explores certain possible programming parameters. With the introduction of multiple independent sources of current and complex lead geometries, the exploration of which parameters to manipulate and how to program them becomes more difficult to express and visualize as well as to set and track. Thus, there is a need to automate and/or facilitate the programming process.

SUMMARY

Disclosed herein is a method for evaluating stimulation therapy in a patient having an electrical stimulator, the method comprising: (a) selecting one or more of a plurality of patient responses (which are examples of clinical indicators) to be used in evaluating stimulation therapy by, determining a first severity of the plurality of the patient responses in the absence of an intervention, determining a second severity of the plurality of the patient responses in the presence of the intervention, and selecting the one or more patient response using the first and second severities, and (b) evaluating the stimulation therapy by, (i) causing the electrical stimulator to apply a set of stimulation parameters to stimulate the patient, (ii) determining a value of each of the selected one or more patient responses in response to applying the set of stimulation parameters, (iii) based on the determined one or more values, adjusting the set of stimulation parameters, and (iv) repeating the steps (i)-(iii) until a stop condition is reached. In other words, the severities of the patient responses with and without the intervention are used to derive one or more patient-specific metrics for evaluating the stimulation therapy. According to some embodiments, the method further comprises assigning a weight to each patient response based on the first and second severity determinations and wherein the selecting the one or more patient response is based on the assigned weights. According to some embodiments, selecting the one or more patient response comprises determining a composite feedback variable (which is an example of a patient-specific metric) that is a mathematical combination of a plurality of patient responses each normalized with its assigned weight. According to some embodiments, the composite feedback variable is a linear combination of more than one patient response, each normalized by its respective weight. According to some embodiments, the intervention comprises providing a pharmaceutical agent to the patient. According to some embodiments, the pharmaceutical agent is levodopa. According to some embodiments, the intervention comprises providing electrical stimulation to the patient. According to some embodiments, the plurality of patient responses comprises one or more of speech, tremor, rigidity, finger tapping, toe tapping, bradykinesia, hypokinesia, agility posture, gate, or postural stability. According to some embodiments, one or more of the plurality of patient responses is determined automatically based on one or more sensors associated with the patient. According to some embodiments, determining the first and second severities comprises ranking the severity of each of the patient responses in the absence and in the presence of the intervention. According to some embodiments, the method further comprises assigning a weight to each patient response based on the rankings of the severity of each of the patient responses in the absence and in the presence of the intervention. According to some embodiments, the stimulation therapy comprises deep brain stimulation. According to some embodiments, the set of stimulation parameters comprises one or more of a stimulation contact configuration, amplitude, frequency, or pulse width.

Also disclosed herein is a computing system for evaluating stimulation therapy in a patient having an electrical stimulator, the system comprising: a processor, and a non-transitory computer readable medium comprising instructions, which when executed by the processor, configure the computing system to: (a) select one or more of a plurality of patient responses to be used in evaluating stimulation therapy by, determining a first severity of the plurality of the patient responses in the absence of an intervention, determining a second severity of the plurality of the patient responses in the presence of the intervention, and selecting the one or more patient response using the first and second severities, and (b) evaluate the stimulation therapy by, (i) causing the electrical stimulator to apply a set of stimulation parameters to stimulate the patient, (ii) determining a value of each of the selected one or more patient responses in response to applying the set of stimulation parameters, (iii) based on the determined one or more values, adjusting the set of stimulation parameters, and (iv) repeating the steps (i)-(iii) until a stop condition is reached. According to some embodiments, selecting one or more of a plurality of patient responses to be used in evaluating stimulation therapy further comprises assigning a weight to each patient response based on the first and second severity determinations and wherein the selecting the one or more patient response is based on the assigned weights. According to some embodiments, selecting the one or more patient response comprises determining a composite feedback variable that is a mathematical combination of a plurality of the patient responses each normalized with its assigned weight. According to some embodiments, the intervention comprises providing a pharmaceutical agent to the patient. According to some embodiments, the intervention comprises providing electrical stimulation to the patient. According to some embodiments, one or more of the plurality of patient responses is determined automatically based on one or more sensors associated with the patient. According to some embodiments, the stimulation therapy comprises deep brain stimulation.

Also disclosed herein are methods of optimizing stimulation for a patient with an implantable pulse generator (IPG), the method comprising: determining one or more patient-specific metrics for the patient based on a plurality of clinical indicators by: assigning a first ranking for each of the clinical indicators based on an evaluation of the clinical indicators for the patient in the absence of a medical intervention, providing the medical intervention to the patient, assigning a second ranking for each of the clinical indicators based on an evaluation of the clinical indicators for the patient in the presence of the medical intervention, determining the one or more patient-specific metrics based on the first and second rankings for each of the clinical indicators, and optimizing the stimulation for the patient using the determined one or more patient-specific metrics. According to some embodiments, optimizing the stimulation for the patient using the determined one or more patient-specific metrics comprises: (i) causing the electrical stimulator to apply stimulation to the patient according to a set of stimulation parameters, (ii) determining a value for the one or more patient-specific metrics, (iii) adjusting the set of stimulation parameters based on the values, and (iv) repeating steps (i) through (iii) until a stop condition based on the values of the patient-specific metrics is reached. According to some embodiments, the one or more patient-specific metrics comprise selected one or more of the clinical indicators. According to some embodiments, the selected one or more of the clinical indicators are selected based on their respective first and second rankings. According to some embodiments, the method further comprises assigning weights to each clinical indicators based on the first and second rankings for each of the clinical indicators. According to some embodiments, the one or more patient-specific metrics comprise a mathematical combination of a plurality of the clinical indicators each normalized using its assigned weight. According to some embodiments, the one or more patient-specific metrics comprise a linear combination of a plurality of the clinical indicators, each normalized by its respective weight. According to some embodiments, the medical intervention comprises providing a pharmaceutical agent to the patient. According to some embodiments, the pharmaceutical agent is levodopa. According to some embodiments, the medical intervention comprises providing electrical stimulation to the patient. According to some embodiments, the plurality of clinical indicators comprises one or more of speech, tremor, rigidity, finger tapping, toe tapping, bradykinesia, hypokinesia, agility posture, gate, or postural stability. According to some embodiments, assigning the first and second rankings for at least one of the clinical indicators is based on measurements from one or more sensors associated with the patient. According to some embodiments, the stimulation therapy comprises deep brain stimulation. According to some embodiments, the stimulation parameters comprise one or more of a stimulation contact configuration, amplitude, frequency, or pulse width.

Also disclosed herein is a system for optimizing stimulation for a patient with an implantable pulse generator (IPG), the system comprising: a processor, and a non-transitory computer readable medium comprising instructions, which when executed by the processor, configure the system to: determine one or more patient-specific metrics for the patient based on a plurality of clinical indicators by: assigning a first ranking for each of the clinical indicators based on an evaluation of the clinical indicators for the patient in the absence of a medical intervention, assigning a second ranking for each of the clinical indicators based on an evaluation of the clinical indicators for the patient in the presence of the medical intervention, and determining the one or more patient-specific metrics based on the first and second rankings for each of the clinical indicators, and optimize the stimulation for the patient using the determined one or more patient-specific metrics. According to some embodiments, optimizing the stimulation for the patient using the determined one or more patient-specific metrics comprises: (i) causing the electrical stimulator to apply stimulation to the patient according to a set of stimulation parameters, (ii) determining a value for the one or more patient-specific metrics, (iii) adjusting the set of stimulation parameters based on the values, and (iv) repeating steps (i) through (iii) until a stop condition based on the values of the patient-specific metrics is reached. According to some embodiments, the one or more patient-specific metrics comprise selected one or more of the clinical indicators. According to some embodiments, the instructions further configure the processor to assign weights to each clinical indicators based on the first and second rankings for each of the clinical indicators. According to some embodiments, the one or more patient-specific metrics comprise a mathematical combination of a plurality of the clinical indicators each normalized using its assigned weight. According to some embodiments, the medical intervention comprises providing a pharmaceutical agent to the patient.

BRIEF DESCRIPTION OF THE DRAWINGS

FIG. 3 shows implantation of the IPG in a patient in a Deep Brain Stimulation (DBS) application.

FIG. 4 shows an electrode lead having segmented electrodes as may be used in a DBS application.

FIG. 5 shows components of a clinician's programmer system, including components for communicating with a neurostimulator such as an IPG.

FIG. 10 shows a listing of patient responses (e.g., symptoms) in a therapy OFF and therapy ON states and a weight associated with the patient responses.

FIGS. 11A-11C show example display screens for evaluating patient symptoms.

FIG. 12 shows an example display screen for selecting symptoms to be used in evaluating stimulation therapy.

DETAILED DESCRIPTION

As mentioned above, current techniques for programming an electrical stimulation system are a tedious trial-and-error process. The instant disclosure relates to methods and systems for automating the programming of electrical stimulation systems, such as the IPG 10 (FIG. 1) used for neuromodulation therapies such as DBS. U.S. Patent Publication No. US 2018/0104500 ("the '500 Application"), published Apr. 19, 2018, entitled "Systems and Methods for Closed-Loop Determination of Stimulation Parameter Settings for an Electrical Simulation System," the entire contents of which are hereby incorporated by reference, describes methods and systems for facilitating the determining and setting of stimulation parameters for programming an electrical stimulation system using closed loop programming. In the system described in the '500 Application, pulse generator feedback logic is executed by a processor to interface with control instructions of an implantable pulse generator by incorporating one or more machine learning engines to automatically generate a proposed set of stimulation parameter values that each affect a stimulation aspect of the implantable pulse generator, receive one or more patient responses (e.g., clinical responses), automatically generate a revised set of values taking into account the received patient responses, and repeat the automated receiving of a patient response and adjusting the stimulation parameter values taking the patient response into account, until or unless a stop condition is reach or the a therapeutic response is indicated within a designated tolerance.

Figure 6:
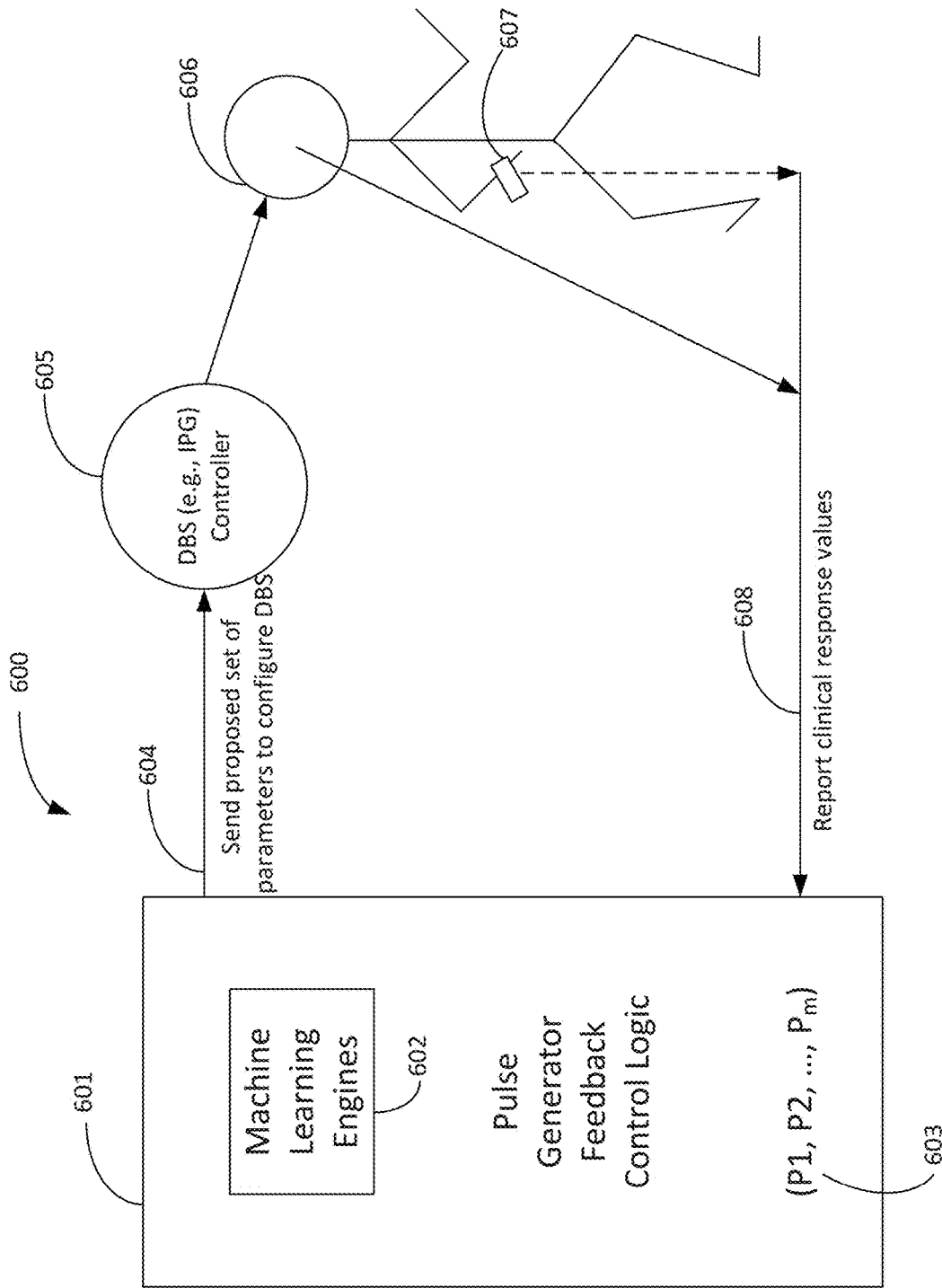
FIG. 6 shows a schematic block diagram for a feedback loop stimulation parameter control system for determining electrical stimulation programming settings.

FIG. 6 illustrates an example feedback loop stimulation parameter control system (FLSPCS) as described in the '500 Application. In at least some embodiments, the FLSPCS 600 includes pulse generator feedback control logic 601 that determines and sends parameters (604) to configure a deep brain stimulator controller 605 (such as IPG 10, FIG. 1). The deep brain stimulator controller 605 then modifies the stimulation parameters of the various leads (such as leads 18 in FIGS. 1, 3, and 4) potentially causing different effects upon the patient 606 in which the IPG is implanted. The patient 606 provides feedback which is reported as patient response values 608 to the pulse generator feedback control logic 601. In some embodiments, the patient 606 provides feedback automatically or semi-automatically via a sensor 607 which are sent to the pulse generator feedback control logic 601 as patient response values 608. According to some embodiments, the feedback is determined by a clinician based on the clinician's observation of the patient. The control logic 601 then adjusts the values of stimulation parameters 603 based upon the received feedback 608 and based upon models implemented by one or more machine learning engines 602. The control logic 601 then sends these adjusted (new or revised) stimulation parameter values (604) to further configure the controller 605 to change the stimulation parameters of the leads implanted in patient 606 to the adjusted values. The feedback-control loop then continues until an outcome is reached that is considered optimal, desired, or acceptable, or until some other stop condition is reached such as number of iterations, time spent in programming session, or the like. An outcome may be considered optimal, desired, or acceptable if it meets certain threshold values or tests (e.g., better outcomes for the patient, faster programming of the device, increased battery life, and/or control multiple independent current sources and directional lead).

Figure 7:
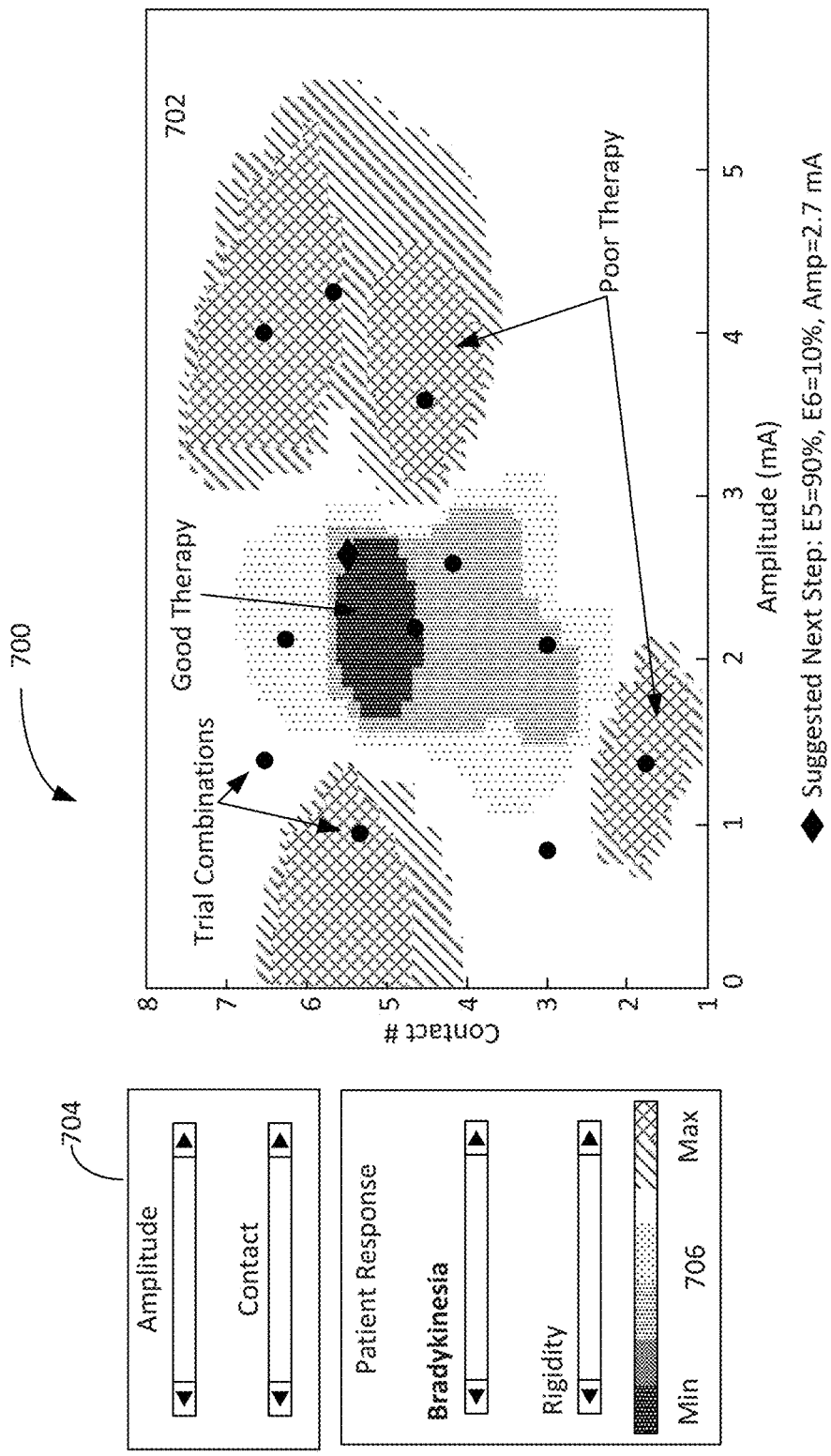
FIG. 7 shows an example display screen for a user interface for visualizing stimulation parameter determinations using a feedback loop stimulation parameter control system.

Aspects of the FLSPCS 600 are described in detail in the incorporated '500 Application and will not be repeated here in detail. However, FIG. 7 is provided for a brief understanding of how the algorithm operates. FIG. 7 illustrates an example of a user interface (UI) 700 that may be operative when a clinician executes an FLSPCS 600 to optimize which electrode contacts to use for stimulation (i.e., which locations to stimulate) and the best amplitude at which to stimulate. Thus, in FIG. 7, the proposed parameters (604, FIG. 6) comprise a contact configuration and an amplitude value. The UI 700 presents a grid 702 with contact numbers (contacts 1-8) on the y-axis and amplitude values on the x-axis. The UI also includes controllers 704 for inputting/adjusting those parameters. The algorithm (i.e., the FLSPCS 600) is configured to suggest proposed parameter values to try. The UI also includes a controller 706 for inputting/recording observed therapeutic responses elicited by the suggested parameters. In FIG. 7, the observed patient response is bradykinesia, which may be measured automatically using a sensor, such as an accelerometer worn by the patient. For example, the patient may be prompted to execute a finger tapping exercise while wearing an accelerometer.

As the algorithm operates, the patient is stimulated with various proposed parameter sets, represented by the blackened circles in the grid 702. The algorithm uses the observed/recorded patient responses to the stimulation and constructs a therapy map within the grid, which represents good therapy (indicated by the shaded areas) and poor therapy (indicated by the crosshatched areas). As the data is collected the algorithm suggests further parameters to try. The next suggested parameter set is indicated by the black diamond in FIG. 7. The algorithm continues until an outcome is reached that is considered optimal, desired, or acceptable, or until some other stop condition is reached such as number of iterations, time spent in programming session, or the like.

Notice that in FIG. 7, the FLSPCS algorithm uses a single patient response, bradykinesia, as the measurable feedback variable for optimizing stimulation. The feedback variable may be selectable from among different feedback variables. The inventor has observed that the selection of one or more appropriate feedback variables can greatly impact the algorithm's ability to optimize therapy for a particular patient. For example, one patient may experience a significant improvement with respect to bradykinesia but another patient may not. However, the other patient may see significant improvement of other symptoms, such as rigidity or tremor. Thus, the methods and systems disclosed in this application can be used to select one or more appropriate feedback variables for optimizing the stimulation parameters. In other words, aspects of the instant disclosure concern determining one or patient-specific metrics that can be used for optimizing a particular patient's stimulation. As described in more detail below, the patient-specific metric may be a weighted combination of multiple patient responses.

Figures 8, 9:
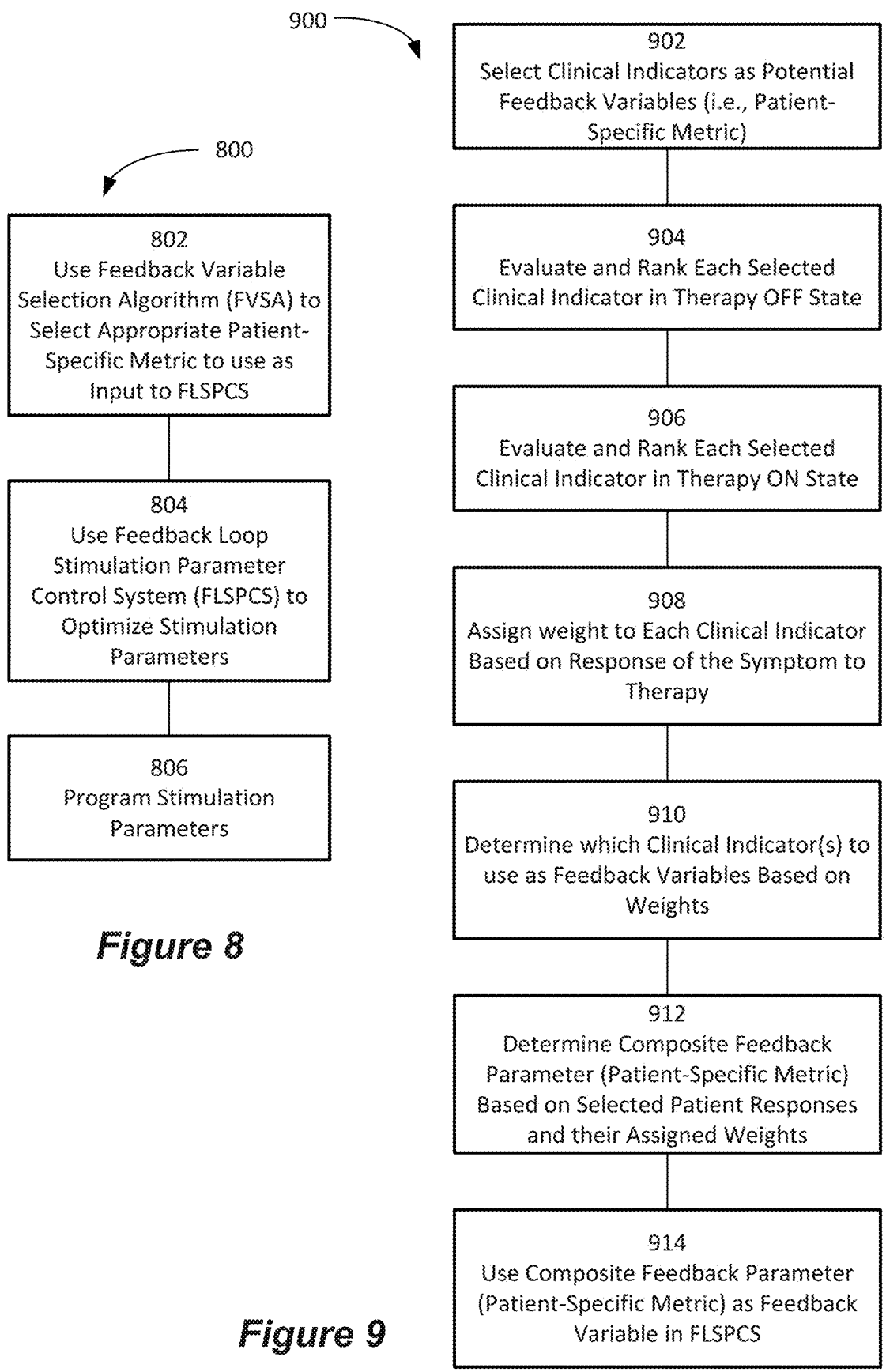
FIG. 8 shows an example workflow for using a feedback variable selection algorithm and a feedback loop stimulation parameter control system to select stimulation programming settings.
FIG. 9 shows an example workflow of a feedback variable selection algorithm.

FIG. 8 illustrates an example of a workflow 800 as disclosed herein. At step 802 a feedback variable selection algorithm (FVSA), as described in further detail below, is used to determine the best patient-specific metric(s) to use as inputs to a stimulation optimization algorithm, such as the FLPCS as described in the '500 Application. At step 804 the FLSPCS is used to determine the optimized stimulation parameters for the patient's therapy. Once the parameters are determined, as step 806 the patient's system is programmed with the optimized stimulation parameters. According to some embodiments, each of the steps shown in FIG. 8 may be performed on an external system capable of programming/controlling the patient's electrical stimulator device. For example, the external system may comprise a clinician's programmer (e.g., 200, FIG. 5) and/or a remote controller (e.g., 40, FIG. 2). According to some embodiments, all three steps may be performed using a clinician's programmer. Alternatively, the external system may include additional computing devices. For example, steps 802 and/or 804 may be performed on a computing device other than a clinician's programmer, such as a tablet, personal computer, smart device, or the like, and a clinician's programmer may be used for step 806. According to some embodiments, some aspects of any of steps 802, 804, and/or 806 may be performed by the patient's stimulator device (e.g., IPG 10, FIGS. 1, 2, 3, and 5). For example, according to some embodiments, aspects of the FVSA and/or FLSPCS may be embodied in the IPG to provide continued optimization of the stimulation parameters outside of the clinical setting.

FIG. 9 illustrates a workflow 900 of an FVSA for selecting one or more appropriate patient-specific metrics to use as input to an algorithm for optimizing stimulation parameters. According to some embodiments, the goal of the FVSA is to identify one or more patient responses (also referred to herein as clinical indicators) or an appropriate combination of patient responses that are expected to respond well to therapy and that therefore provide good feedback variables for optimizing stimulation settings. The clinical indicators may comprise patient symptoms, a therapeutic response, or the like. In other words, the goal of the FVSA is to identify one or more patient-specific metrics for optimizing therapy for the particular patient.

Step 902 in the workflow comprises identifying possible clinical indicators to evaluate. According to some embodiments, the clinical indicators may be selected from among a standard battery of tests used for diagnosing neurological disorders, such as motor responses prescribed by the UPDRS (e.g., UPDRS-Part III), which is known in the art. Other examples may include movement disorders UPDRS (MDS-UPDRS), and/or readings from sensors with an arbitrary scale. Examples of clinical indicators that might be evaluated include speech, tremor at various anatomical locations, rigidity at various anatomical locations, the ability to perform tasks such as finger tapping or toe tapping, bradykinesia/hypokinesia, agility, posture, gate, postural stability, and the like. It should be recognized that some clinical indicators are axial, i.e., they are not confined to the left or right side of the body. Other clinical indicators are left- or right-side specific. The selected clinical indicators will make up the universe of possible clinical indicators that will be evaluated as potential patient-specific metrics.

Once the universe of clinical indicators is determined the severity of each clinical indicator is evaluated in a therapy OFF state and the therapy ON state to determine how each clinical indicator responds to therapy. The therapy OFF state is simply the absence of any therapeutic intervention. According to some embodiments, the therapy ON state may be the provision of stimulation (e.g., DBS). As an example of DBS that may be provided as the therapy ON state, commonly, a monopolar review is performed as first step to define the initial stimulation parameters. The monopolar review consists on activating each contact independently with fixed pulse widths and frequency (for example, 60 μs and 130 Hz, respectively) and increasing the stimulation amplitude (either current or voltage) until side effects and therapy (commonly rigidity suppression) thresholds are determined. The contacts yielding the largest therapeutic window (difference between side effect and therapy thresholds) are commonly used for the initial stimulation.

Additionally (or alternatively), the therapy ON state may be the provision of a pharmaceutical intervention, such as levodopa. For example, it is recognized that clinical indicators that respond well to levodopa often also respond well to DBS. Often, patients that are considered possible candidates for DBS implantation undergo a "Levodopa Challenge," to determine how their clinical indicators respond to levodopa. Thus, a patient's Levodopa Challenge results may be used to determine appropriate clinical indicators to use as patient-specific metrics.

The illustrated example workflow comprises evaluating clinical indicators in the therapy OFF state (step 904, below) first and then evaluating clinical indicators in the therapy ON state (step 906, below). However, it should be appreciated that those steps could be performed in reverse order.

At step 904 of the workflow 900, the severity of each of the clinical indicators are evaluated and ranked in a therapy OFF state. In other words, the severity of each of the clinical indicators are evaluated while the patient is not subjected to any intervention (such as stimulation or pharmaceutical intervention), to determine a baseline ranking of each clinical indicator. Note that "ranking" does not necessarily imply "sorting" the clinical indicators least to most severe, but more typically means assigning each indicator its own independent ranking value based on the severity of that clinical indicator. According to some embodiments, the clinical indicators may be ranked numerically based on the severity of the clinical indicator. For example, as in the UPDRS-Part III, the clinical indicators may be ranked on a scale of 0 to 4, with 0=Normal; 1=slight; 2=mild; 3=moderate; and 4=severe. Other ranking scales may be used depending on the specific implementation of the workflow 900. The clinical indicators may be ranked based on patient feedback and/or clinical observation as well as based on sensor measurements. According to some embodiments, a combination of measurement criteria is used. For example, the severity of some clinical indicators may be ranked based on observation while others are ranked based on sensor readings. According to some embodiments, the evaluation of the therapy OFF clinical indicators may be obtained from pre-operative Levodopa challenge evaluations of the patient.

At step 906 of the workflow 900, the severity of each of the clinical indicators are evaluated and ranked in a therapy ON state. Again, the therapy ON state may comprise the provision of stimulation, such as DBS. Alternatively (or additionally), the therapy ON state may comprise the provision of pharmaceutical treatment, such as levodopa. According to some embodiments, the evaluation of the therapy ON clinical indicators may be obtained from preoperative Levodopa challenge evaluations of the patient.

At step 908 of the workflow 900, a weight is assigned to each of the clinical indicators based on the difference between the clinical indicator's ranking in the therapy OFF state and in the therapy ON state. In other words, the weight assigned to a clinical indicator indicates how well the clinical indicator responds to the therapy. According to some embodiments, the clinical indicators may be weighted based on a mathematical analysis, such as a principal component analysis PCA. According to other embodiments, other weighting algorithms may be used.

FIG. 10 illustrates an example of clinical indicators measured and ranked in therapy OFF and therapy ON states and weights assigned to each clinical indicator. In FIG. 10, weights were assigned to clinical indicators according to the following rules: (1) if the ranking for the clinical indicator in the therapy OFF state is 0, then the clinical indicator is ignored (i.e., no rating is assigned); (2) if the ranking for the clinical indicator in the therapy OFF state is >0, then the weighting factor W is determined by $W=(R_{T-OFF}-R_{T-ON})^2/(X \cdot R_{T-OFF})$, where $R_{T-OFF}$ and $R_{T-ON}$ are the rankings of the clinical indicator in the therapy OFF and ON states, respectively, and X is the value of the most severe possible ranking of the clinical indicator. In the illustrated example, a ranking of 4 corresponds to the most severe clinical indicator, and thus, X=4 in the illustrated example. This weighting formula considers both the magnitude of improvement and the end state of the clinical indicator in the presence of therapy. In other words, according to the weighting formula, an improvement that results in an absence of the clinical indicator should be ranked higher than an improvement that results in the clinical indicator still being present. For example, notice in FIG. 10 that both speech and facial expression, which improved from a ranking of 3 in the absence of therapy to a 1 in the presence of therapy (an overall improvement of 2 ranking points) was assigned a weight of 0.333. However, facial tremor, which improved from a ranking of 2 to a ranking of 0 (also an overall improvement of 2 ranking points) was assigned a weight of 0.500. Facial tremor was assigned a higher weight because therapy resulted in a complete absence of the symptom.

According to some embodiments, the user (e.g., a clinician) can manually modify/edit or assign the weighting factor associated with the clinical indicators. For example, a particular clinician may prefer certain clinical indicators as feedback variables and may choose to weight those clinical indicators higher than the weighting factor determined by the formula. According to some embodiments, the weights or the clinical indicators may be increased if the improvement found during the stimulation setting optimization session is greater than the improvement measured at the before the session. For instance, if in the absence of treatment, rigidity score was 4 and with treatment, that score went to 1, that would result in a weight of 0.75. However, if during the stimulation settings optimization session, a stimulation setting achieved a rigidity score of 0, which would result in a weight of 1. Therefore, the weights of all the selected symptoms should be updated to reflect the potential benefit of that stimulation setting for rigidity.

Notice the list of clinical indicators illustrated in FIG. 10 includes four clinical indicators that were measured using a sensor, such as an accelerometer, worn by the patient (illustrated in shaded boxes in FIG. 10). Again, any number of clinical indicators may be considered, and they may be sensor-based, observation-based, or a combination of the two.

Referring again to FIG. 9, at step 910 the workflow 900 may select which clinical indicators to use as patient-specific metrics. The selection may be determined based on the weights assigned in step 908. For example, all clinical indicators with a weight exceeding a pre-defined threshold value may be selected. Alternatively, a user may manually select the clinical indicators to use as patient-specific metrics.

At step 912, the workflow 900 may determine a composite feedback parameter based on the selected clinical indicators. For example, a composite feedback parameter may be determined as a linear combination of the selected clinical indicators, each weighted by their assigned weights. The determined composite feedback parameter can be used as a patient-specific metric for optimizing stimulation parameters, for example, using a FLSPCS, as described in the '500 Application (Step 912).

Figure 11A:
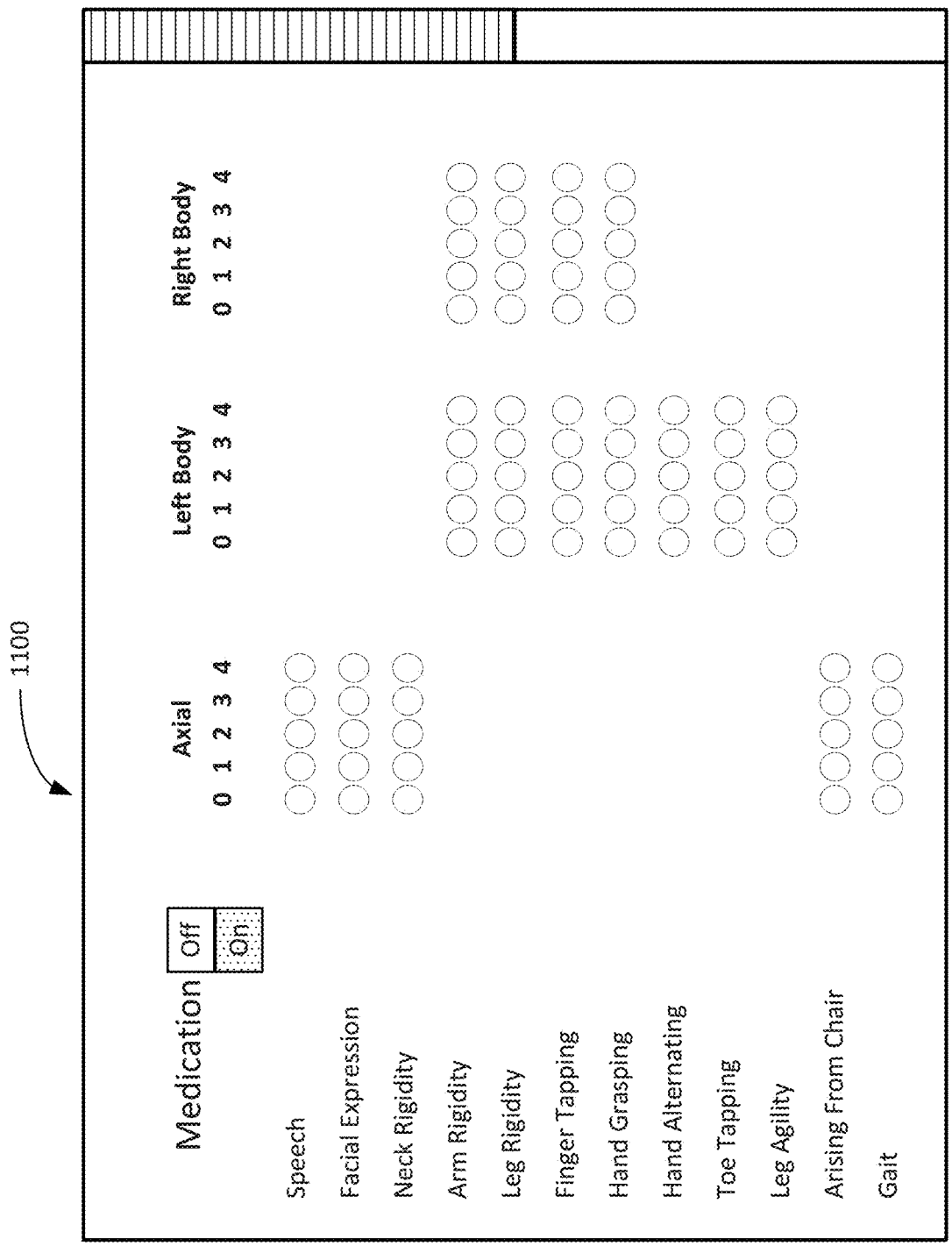
Figure 11B:
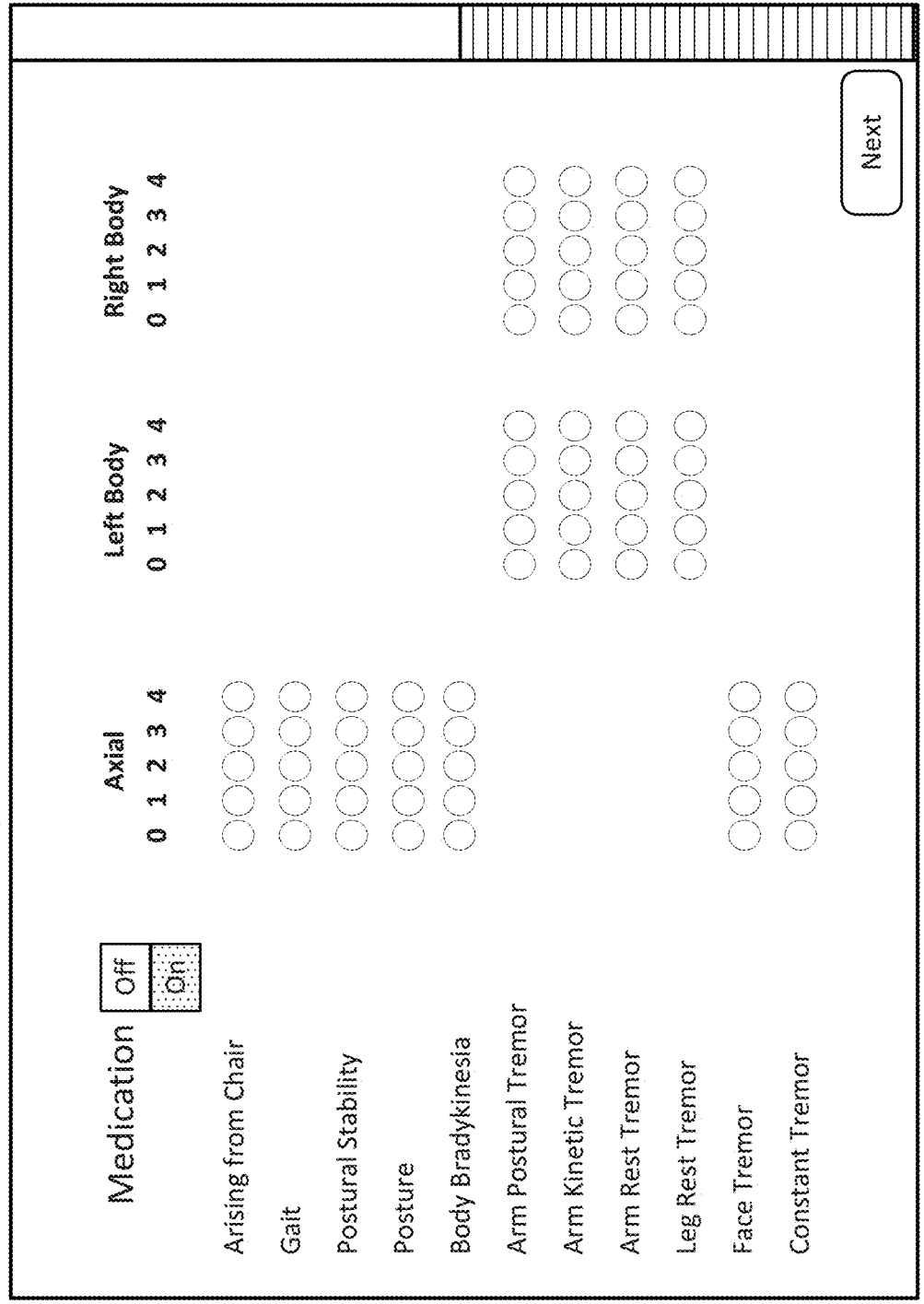

According to some embodiments, the disclosed methods and systems provide a menu-driven UI for evaluating the patient's clinical indicators in the therapy OFF and ON states. FIGS. 11A and 11B illustrate a page 1100 of a UI that allows a clinician to rank the patient's clinical indicators in the therapy/medication OFF and ON states. The UI page provides a list of various clinical indicators to evaluate (Step 902 of FIG. 9). As mentioned above, one or more of the patient's responses may be measured automatically using one or more sensors, such as accelerometers or the like. Thus, the system may provide a UI page, such as illustrated in FIG. 11C for selecting which clinical indicators to measure using a sensor.

The clinician can use the page 1100 (FIGS. 11A and 11B) to evaluate the patient's clinical indicators in the therapy OFF and therapy ON states (Steps 904 and 906, FIG. 9). Upon the completion of the two evaluations, the system can assign weights to each clinical indicator (Step 908, FIG. 9), based on the improvement between the two states, similar to the list of weights reflected in FIG. 10. As described above, the weights may be determined based on one or more mathematical operations, such as PCA or other mathematical formulas. The list of weights determined for each clinical indicator may be printed as a report (similar to the list shown in FIG. 10) or may be reflected on a screen of the UI.

Once weights are determined for each of the clinical indicators, the UI may provide a screen 1200, as shown in FIG. 12, which allows the user (e.g., a clinician) to select which clinical indicators to include in a composite patient-specific metric for optimizing stimulation settings. According to some embodiments, different clinical indicators may be chosen as patient-specific metrics for programming different electrode leads, for example, for programming left and right hemisphere leads. According to some embodiments, one or more clinical indicators may be auto-populated into the screen 1200, for example if the clinical indicator's weight exceeds a certain threshold. According to some embodiments, the user may select clinical indicators to include in the composite patient-specific metric from a drop-down menu, for example. According to some embodiments, the user may select as many or as few clinical indicators as desired.

According to some embodiments, the screen 1200 may also reflect the weight assigned to each clinical indicator. The weight may be the weight determined mathematically and/or from PCA or other methods, as described above, and may be auto-populated into the screen 1200. According to some embodiments, the user may be able to adjust the assigned weight, based on user experience or other factors.

Figure 13:
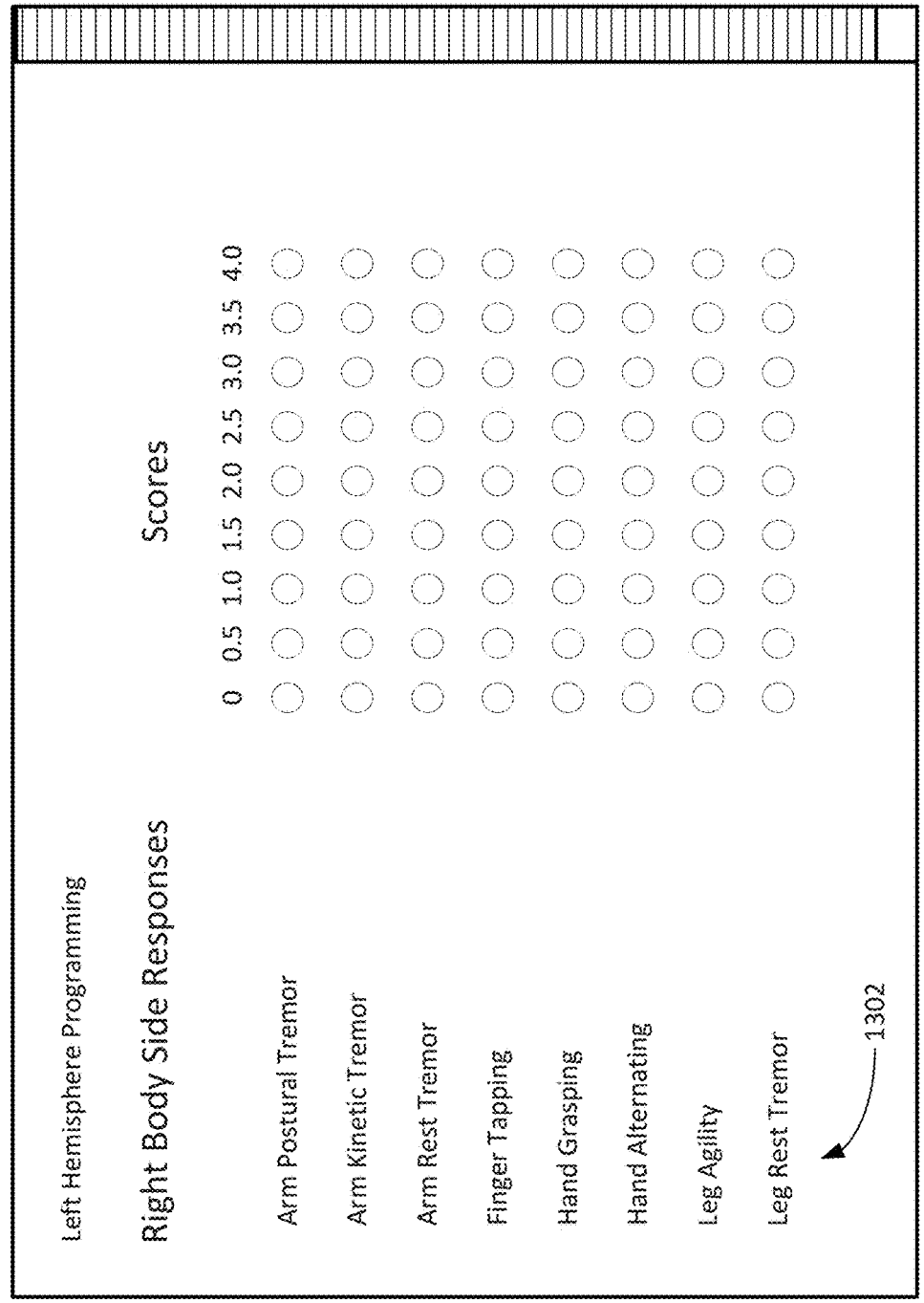
FIG. 13 shows an example display screen for ranking patient responses during the evaluation of stimulation therapy.

Once the user has selected the clinical indicators to include in a composite patient-specific metric for optimizing stimulation settings, the UI may present a screen 1300 as shown in FIG. 13. For example, assume that the user (i.e., the clinician) has selected clinical indicators 1302 as component clinical indicators included in the composite patient-specific metric for programming a lead in the left hemisphere of the patient's brain. The clinician would then use a feedback loop stimulation parameter control system (FLSPCS) as described in the '500 Application to determine candidate stimulation settings for programming stimulation at the lead, as described below.

Figure 14:
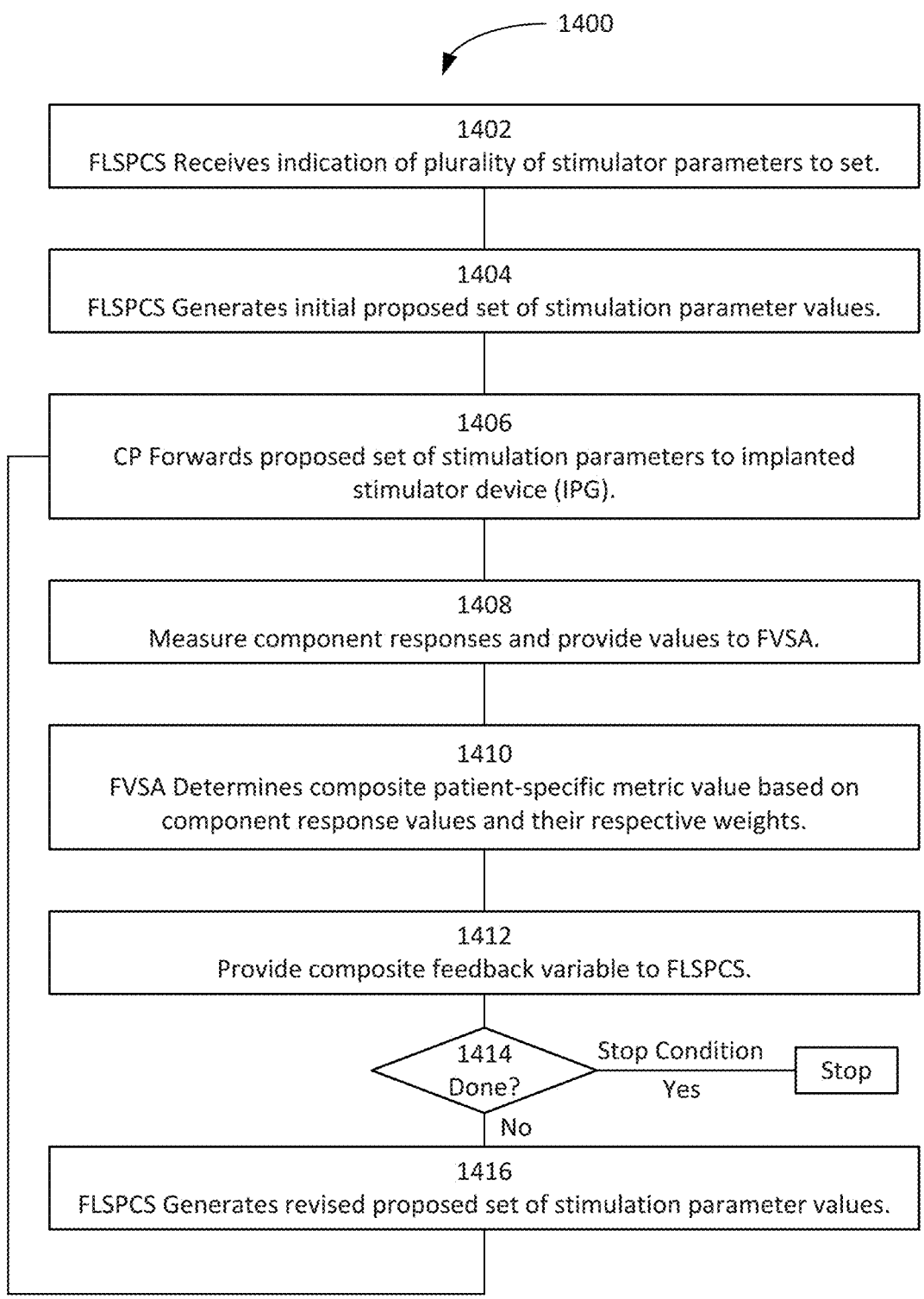
FIG. 14 shows an example of a workflow for using a feedback variable selection algorithm and a feedback loop stimulation parameter control system to select stimulation programming settings.

FIG. 14 illustrates a workflow 1400 that a user can implement to determine stimulation settings using a screen 1300 of a FVSA algorithm as described above, a FLSPCS as described in the '500 Application, and the stimulator control UI options of the clinician's programmer. As mentioned above, the FVSA algorithm, the FLSPCS algorithm and the associate UI options may be implemented as modules on the same computing device, such as the clinician's programmer. Alternatively, one or more of the FVSA/FLSPCS may be implemented on a separate computing device and the clinician may simply use the clinician programmer to transmit the stimulation parameters determined by the FVSA/FLSPCS to the implanted stimulator device.

At step 1402 the FLSPCS receives an indication of a plurality of stimulation parameters to set. For example, the set of stimulation parameters being adjusted may comprise contact locations, amplitude, frequency, pulse width, and the like. Directional leads may include additional parameters such as x, y, and z coordinates, angle, and shape. Other parameters and parameterizations are discussed in the incorporated '500 Application.

At step 1404 the FLSPCS generates an initial proposed set of stimulation parameter values. These include a value for each stimulation parameter being adjusted. For example, when the set of stimulation parameters include contact location and amplitude, the initial proposed set may be "contact=3" and "amplitude=2 mA," etc. In one example embodiment, the initial proposed set of stimulation parameter values is chosen arbitrarily because data has not been collected yet for this patient. In another example embodiment, the logic is expanded to use the distribution of optimal settings (e.g. amplitude and/or contact location) from previous patients to pick the starting setting for a new patient. This allows clinicians to begin the programming session with settings that other patients have found beneficial. In addition, new patients may be matched to previous patients via external information, such as diagnosis, imaging data, or baseline clinical indicator severity.

At step 1406 the user forwards the proposed set of stimulation parameters to the implanted electrical stimulator device, typically using the clinician's programmer. At step 1408, the component clinical indicators of the composite patient-specific metric are ranked and the ranking values are provided to FVSA, for example, using a screen such as screen 1300 (FIG. 13). According to some embodiments, the clinician may wait for a time period before ranking the component clinical indicators to account for any "wash in" period for the applied stimulation.

At step 1410 the FVSA can determine a composite patient-specific metric value based on the determined rankings of the each of the component clinical indicators and the weights assigned for each of the clinical indicators. At step 1412, the determined composite patient-specific metric is provided to the FLSPCS. At step 1414, the logic of the FLSPCS determines whether an end condition is reached. For example, the logic may determine whether the composite patient-specific metric is within a designated threshold. In some embodiments, other stop conditions are designated such as a certain number of iterations has been performed, the therapeutic response changes less than x % with y number of iterations, or the user is satisfied with the result. Other stop conditions are possible. If the stop condition is reached, then the process stops.

If the stop condition is not reached, then at step 1416 the FLSPCS generates a revised proposed set of stimulation parameter values. The process defined in steps 1406-1412 are then repeated. The workflow 1400 may be iteratively repeated until an appropriate stop condition is reached.

As the workflow 1400 is iteratively repeated, the FLSPCS may construct and display a therapy map, similar to the therapy map 702 shown in FIG. 7. Recall that in the therapy map 702, a single therapeutic response (bradykinesia, in the case of 702) is mapped as a function of stimulation settings. In the embodiments using a FVSA, such as the workflow 1400, the therapy map is based on the determined composite patient-specific metric responses, which can be mapped as a function of stimulation settings. According to some embodiments, maps for the individual clinical indicators may also be constructed, though this embodiment is not illustrated. According to some embodiments, based on the therapy maps, stimulation settings considering different target regions may be suggested. For instance, if rigidity is best treated when electrode 1 is activated at 3 mA but this setting is not best for finger tapping, for which the activation of electrode levels 3 and 4 with a current distribution of 40% and 60%, respectively is the best with a total current of 2 mA, then the FLSPCS could suggest as stimulation setting equivalent to a combination of the activation of electrodes 1 and levels 3 and 4

Figure 15:
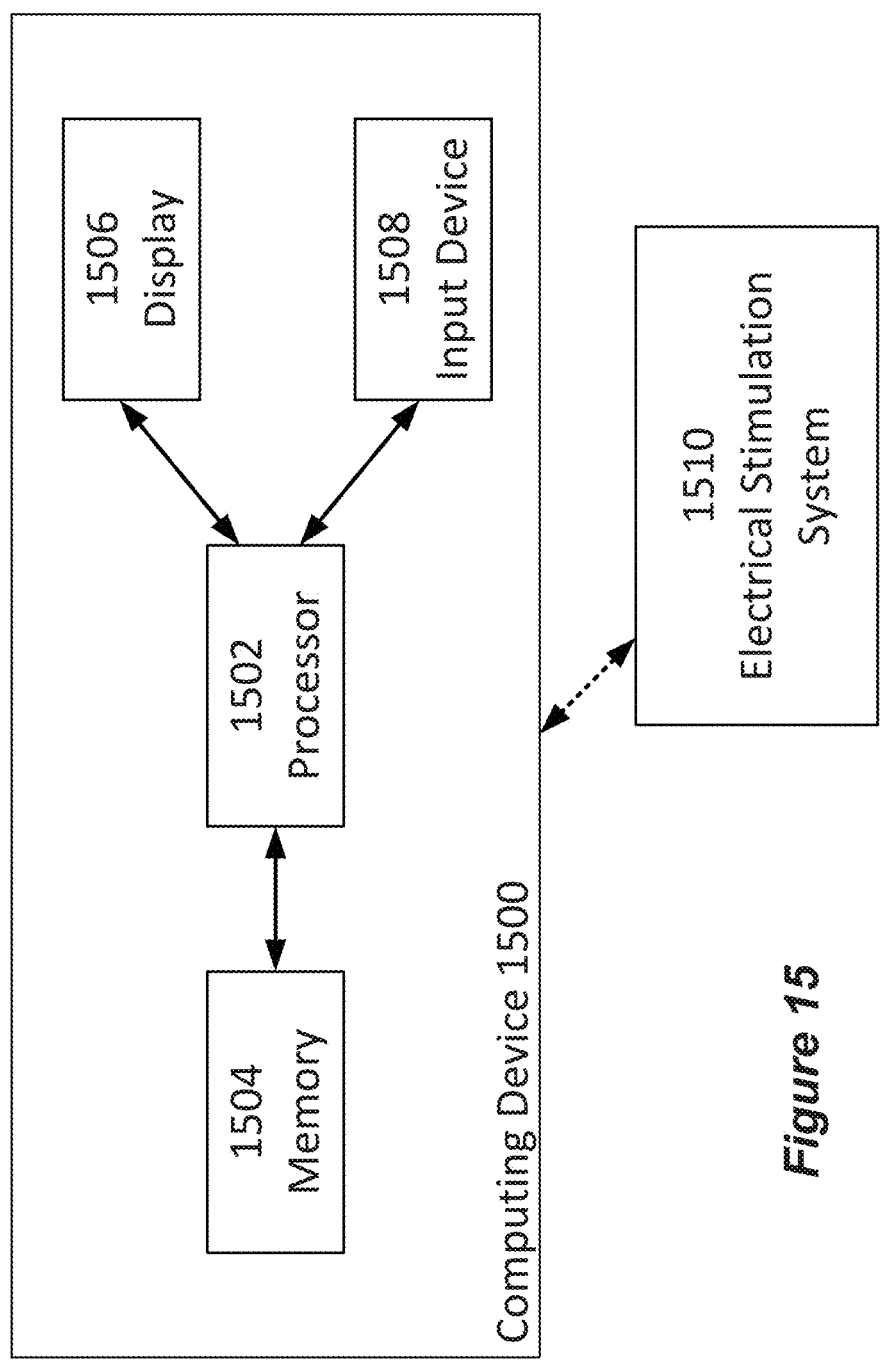
FIG. 15 shows a schematic block diagram of one embodiment of a computing system for programming an electrical stimulation system.

As mentioned above, the methods, systems, and algorithms (such as the FVSA) for determining an appropriate patient-specific metric, such as a composite patient-specific metric for optimizing stimulation settings may be implemented on a computing device, which may be a clinician's programmer or may be separate from the clinician's programmer. FIG. 15 illustrates one embodiment of a computing device 1500 for running the software, hardware, or firmware embodiments of a FVSA. According to some embodiments, the computing device may also be configured for running the software, hardware, or firmware embodiments of a stimulation parameter feedback loop control system, such as described in the '500 Application. The computing device 1500 includes a processor 1502 and a memory 1504, a display 1506, and an input device 1508. Optionally, the computing device 1500 may be connected to or otherwise integrated with the electrical stimulation system 1510 (which may include the components illustrated in FIGS. 1, 2, and 5). For example, in some embodiments, the computing device 1500 is part of the electrical stimulation system 1510, such as part of the clinician programmer 200 (FIG. 5), remote control 40 (FIG. 2), or external trial stimulator (not illustrated). In other embodiments, the computing device 1500 is separate from the electrical stimulation system 1510.

The computing device 1500 can be a computer, tablet, mobile device, or any other suitable device for processing information. The computing device 1500 can be local to the user or can include components that are non-local to the computer including one or both of the processor 1502 or memory 1504 (or portions thereof). For example, in some embodiments, the user may operate a terminal that is connected to a non-local processor or memory.

Figure 1:
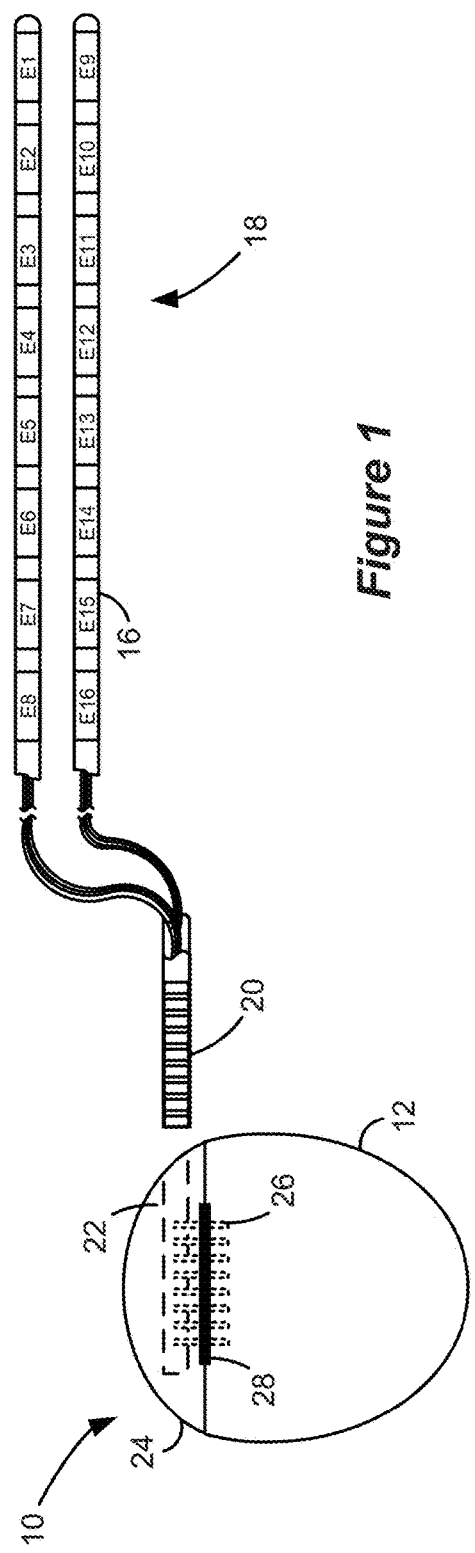
FIG. 1 shows an implantable pulse generator (IPG) with an electrode array.
Figure 2:
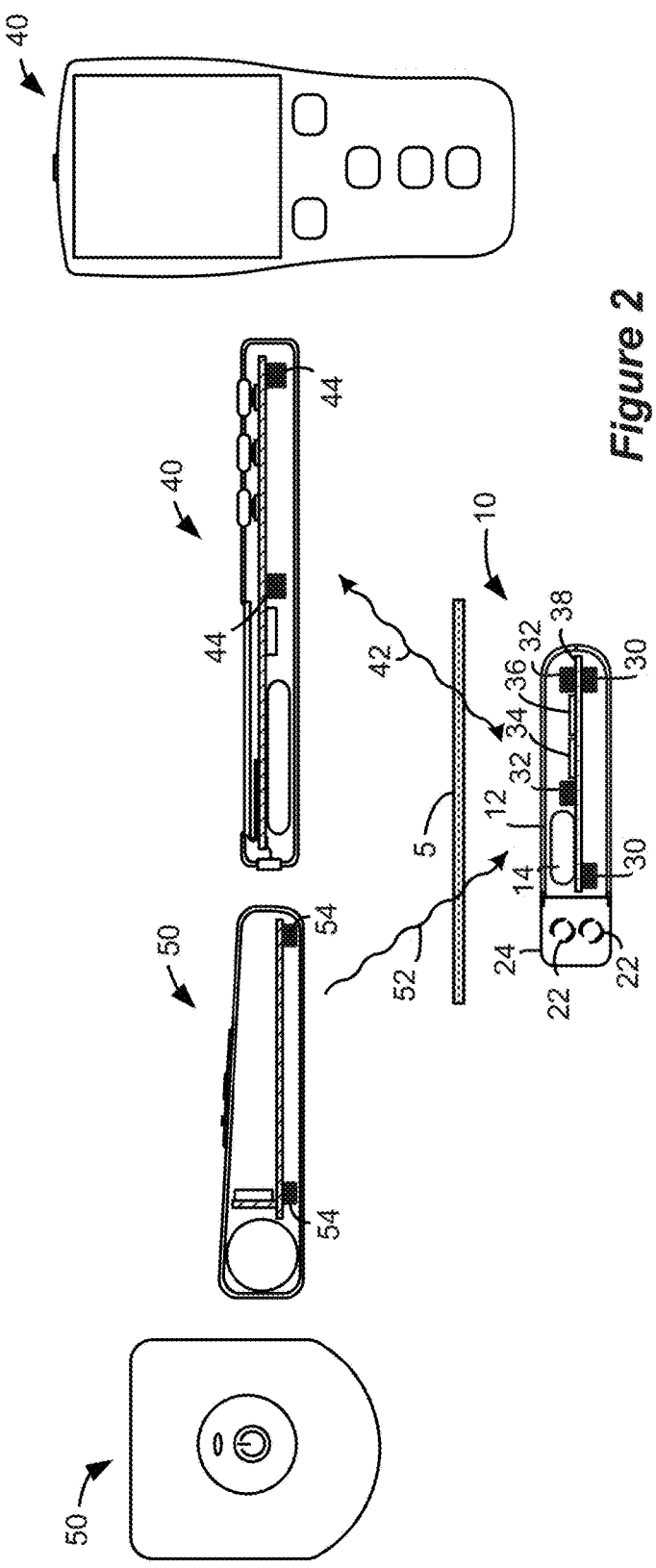
FIG. 2 shows a cross section of the IPG of FIG. 1 as implanted in a patient, as well as external devices that support the IPG, including an external charger and external controller.

Other examples of computing devices can include a watch, wristband, smart phone, or the like. Such computing devices can wirelessly communicate with the other components of the electrical stimulation system, such as the clinician programmer 200 (FIG. 5), remote control 40 (FIG. 2), external trial stimulator (not illustrated), or IPG 10 (FIG. 1). Such devices may also be useful for gathering patient information, such as general activity level or present queries or tests to the patient to identify or score pain, depression, stimulation effects or side effects, cognitive ability, or the like. For example, the device may ask the patient to take a periodic test (for example, every day) for cognitive ability to monitor, for example, Alzheimer's disease. Such devices may also be used to sense clinical indicators to therapy such as, for example, tremor, heart rate, or the like. The device may communicate with the clinician programmer 200 (FIG. 5), remote control 40 (FIG. 2), external trial stimulator (not illustrated), or IPG 10 (FIG. 1) to direct changes to the stimulation parameters using a closed loop algorithm, as described below, which may be on the device or the IPG. This device could be given to the patient to wear only during programming sessions; or, it could be worn all of the time and continually adjust the stimulation parameters. The algorithm could be on the patient's phone, which is connected to the IPG and possibly an evaluating device (e.g. a wristband or watch), to make changes to the stimulation parameters. These devices may also be used to record and send information to the clinician.

The computing device 1500 can utilize any suitable processor 1502 including one or more hardware processors that may be local to the user or non-local to the user or other components of the computing device. The processor 1502 is configured to execute instructions provided to the processor.

Any suitable memory 1504 can be used for the computing device 1500. The memory 1504 illustrates a type of computer-readable media, namely computer-readable storage media. Computer-readable storage media may include, but are not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 1506 can be any suitable display or presentation device, such as a monitor, screen, display, or the like, and can include a printer. The input device 1508 can be, for example, a keyboard, mouse, touch screen, track ball, joystick, voice recognition system, or any combination thereof, or the like. Another input device 1508 can be a camera from which the clinician can observe the patient. Yet another input device 1508 is a microphone where the patient or clinician can provide responses or queries.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing stimulation to the brain of a patient for the treatment of Parkinson's Disease (PD) using an implantable pulse generator (IPG) and one or more electrode leads implanted in the patient's brain, wherein each electrode lead comprises a plurality of electrodes configured to contact the patient's brain, the method comprising:
   determining one or more patient-specific metrics for the patient from a plurality of potential clinical indicators indicative of PD by:
      assigning a first ranking for each of the clinical indicators based on an evaluation of the clinical indicators for the patient in the absence of a medical intervention,
      providing the medical intervention to the patient,
      assigning a second ranking for each of the clinical indicators based on an evaluation of the clinical indicators for the patient in the presence of the medical intervention,
      determining the one or more patient-specific metrics based on the first and second rankings for each of the clinical indicators, and
   determining optimized stimulation parameters for the patient using the determined one or more patient-specific metrics, and
   using the IPG to provide therapeutic stimulation to the patient using the optimized stimulation parameters, wherein the therapeutic stimulation is configured to reduce symptoms of PD in the patient.

2. The method of claim 1, wherein determining optimized stimulation parameters for the patient using the determined one or more patient-specific metrics comprises:
   (i) causing the IPG to apply stimulation to the patient according to a set of stimulation parameters,
   (ii) determining a value for each of the one or more patient-specific metrics,
   (iii) adjusting the set of stimulation parameters based on the values, and
   (iv) repeating steps (i) through (iii) until a stop condition based on the values of the patient-specific metrics is reached.

3. The method of claim 1, wherein the one or more patient-specific metrics comprise selected one or more of the clinical indicators.

4. The method of claim 3, wherein the selected one or more of the clinical indicators are selected based on their respective first and second rankings.

5. The method of claim 1, further comprising assigning weights to each of the clinical indicators based on the first and second rankings for each of the clinical indicators.

6. The method of claim 5, wherein the one or more patient-specific metrics comprise a mathematical combination of a plurality of the clinical indicators each normalized using its assigned weight.

7. The method of claim 5, wherein the one or more patient-specific metrics comprise a linear combination of a plurality of the clinical indicators, each normalized by its respective weight.

8. The method of claim 1, wherein the medical intervention comprises providing a pharmaceutical agent to the patient.

9. The method of claim 8, wherein the pharmaceutical agent is levodopa.

10. The method of claim 1, wherein the medical intervention comprises providing electrical stimulation to the patient.

11. The method of claim 1, wherein the plurality of clinical indicators comprises one or more of speech, tremor, rigidity, finger tapping, toe tapping, bradykinesia, hypokinesia, agility, posture, gait, or postural stability.

12. The method of claim 1, wherein assigning the first and second rankings for at least one of the clinical indicators is based on measurements from one or more sensors associated with the patient.

13. The method of claim 1, wherein the therapeutic stimulation therapy comprises deep brain stimulation.

14. The method of claim 2, wherein the stimulation parameters comprise one or more of a stimulation contact configuration, amplitude, frequency, or pulse width.

15. A system for optimizing stimulation for a patient with an implantable pulse generator (IPG) to treat symptoms of Parkinson's Disease (PD) in the patient, the system comprising:
  a processor, and
  a non-transitory computer readable medium comprising instructions, which when executed by the processor, configure the system to:
    determine one or more patient-specific metrics for the patient based on from a plurality of potential clinical indicators indicative of PD by:
      assigning a first ranking for each of the clinical indicators based on an evaluation of the clinical indicators for the patient in the absence of a medical intervention,
      assigning a second ranking for each of the clinical indicators based on an evaluation of the clinical indicators for the patient in the presence of the medical intervention, and
      determining the one or more patient-specific metrics based on the first and second rankings for each of the clinical indicators, and
    optimize the stimulation for the patient using the determined one or more patient-specific metrics, and
    cause the IPG to provide therapeutic stimulation to the patient using the optimized stimulation, wherein the therapeutic stimulation is configured to reduce symptoms of PD in the patient.

16. The system of claim 15, wherein optimizing the stimulation for the patient using the determined one or more patient-specific metrics comprises:
  (i) causing the IPG to apply stimulation to the patient according to a set of stimulation parameters,
  (ii) determining a value for each of the one or more patient-specific metrics,
  (iii) adjusting the set of stimulation parameters based on the values, and
  (iv) repeating steps (i) through (iii) until a stop condition based on the values of the patient-specific metrics is reached.

17. The system of claim 15, wherein the one or more patient-specific metrics comprise selected one or more of the clinical indicators.

18. The system of claim 15, wherein the instructions further configure the processor to assign weights to each of the clinical indicators based on the first and second rankings for each of the clinical indicators.

19. The system of claim 18, wherein the one or more patient-specific metrics comprise a mathematical combination of a plurality of the clinical indicators each normalized using its assigned weight.

20. The system of claim 15, wherein the medical intervention comprises providing a pharmaceutical agent to the patient.

* * * * *